United States Patent [19]

Wohltjen

[11] 4,312,228
[45] Jan. 26, 1982

[54] METHODS OF DETECTION WITH SURFACE ACOUSTIC WAVE AND APPARATI THEREFOR

[76] Inventor: Henry Wohltjen, 181 E. Lake Blvd., Mahopac, N.Y. 10451

[21] Appl. No.: 62,019

[22] Filed: Jul. 30, 1979

[51] Int. Cl.$^3$ ............................................ G01N 29/00
[52] U.S. Cl. ........................................ 73/597; 73/23; 73/599; 310/313 R
[58] Field of Search ................... 73/596, 597, 599, 23, 73/23.1, 24; 310/313 R

[56] References Cited

U.S. PATENT DOCUMENTS

| | | | |
|---|---|---|---|
| 3,164,004 | 1/1965 | King | 73/23 |
| 3,557,605 | 1/1971 | Lannean et al. | 73/24 |
| 4,055,072 | 10/1977 | Fletcher | 73/23 |

OTHER PUBLICATIONS

"Using Quartz Crystals as Sorption Detectors" by King from Research/Development, 20 (4 & 5), at 28 (1969).
"Surface Acoustic Wave Film Thickness Monitor" by Kovnovich et a., from Rev. of Sci. Instr., 48 (7) at 920 (1977).
"Non–Destructive Testing of Thin Films by Harmonic Generation of Dispersive Rayleigh Waves", by Lean et al. App. Physics Lett., 19 (9) at 356 (1971).
"Acoustic Surface Wave Attenuation. . ." by Jain from Acoustic Surface Wave and Acousto-optic Devices, Optonsonic Press, New York, 63 (1971).
"Attenuation of Microwave Acoustic Surface Waves Due to Gas Loading"by Slobodnik from J. of Applied Physics, 43 (6) at 2565 (1972).

Primary Examiner—James J. Gill
Attorney, Agent, or Firm—Curtis, Morris & Safford

[57] ABSTRACT

The invention is in the monitoring of physical parameters relating to various fluids and polymers by contacting same with the surface of a piezoelectric material unit through which is passing a surface acoustic wave, and measuring the alteration of that wave as an indication of these parameters. The invention is also in apparati for monitoring certain of said parameters.

16 Claims, 15 Drawing Figures

METHODS OF DETECTION WITH SURFACE ACOUSTIC WAVE AND APPARATI THEREFOR

FIELD OF THE INVENTION

The invention is in the monitoring of physical parameters relating to various fluids and polymers by contacting same with the surface of a piezoelectric material unit through which is passing a surface acoustic wave, and measuring the alteration of that wave as an indication of these parameters. The invention is also in apparti for monitoring certain of said parameters.

DESCRIPTION OF THE PRIOR ART

Despite the ever-present demand for analysis methods and apparati which are less expensive and more convenient to operate, surface acoustic wave devices as physical probes have received little attention in the literature. The use of a quartz surface acoustic wave resonator as a film thickness monitor for vacuum deposition systems is reported in Kovnovich, S. and Harnik, E., "Surface Acoustic Wave Film Thickness Monitor", *Rev. Sci. Instrum.,* 48 (7), at 920 (1977). The velocity of propagation of the wave is altered as a function of the thickness of a metal film on the surface acoustic wave resonator, thereby changing the resonance of an oscillator controlled by the device. The use of a surface acoustic wave apparatus to evaluate elastic properties of thin metal films is reported in Lean, E. G. and Powell, C. G., "Non-destructive Testing of Thin Films by Harmonic Genertion of Dispersive Raleigh Waves." *Appl. Phys. Lett.,* 19 (9), at 356 (1971). A very sophisticated laser optical probing system was employed to monitor the generation of higher order harmonic waves in the film. The utilization of a surface acoustic wave delay line to monitor the attenuation produced in the wave by a thin, super-conducting metal film is reported in Jain, M. C., "Acoustic Surface Wave Attenuation Studies in Superconducting Thin Film Systems", *Acoustic Surface Wave and Acousto-Optic Devices,* Optosonic Press, New York 63 (1971). None of the foregoing are addressed to surface acoustic wave alteration merely by interaction of a substance, e.g., a fluid component, with a piezoelectric material coated with a suitably interactive material. Nor is any of the foregoing addressed to measurement of changes of, for example, thermomechanical properties of a polymer in contact with a surface acoustic wave device merely by changing the polymer's environment.

The investigation of the effect of gas-loading on attenuation of a surface wave in an uncoated piezoelectric material was reported in Slobodnik, A. F., "Attenuation of Microwave Acoustic Surface Waves Due to Gas Loading," *J. Appl. Phys.,* 43 (6), at 2565 (1972). Attenuation was found to be a function of gas pressure. However, there is no indication in the foregoing that interaction of a substance, e.g., a fluid component, with a coating on a piezoelectric material alters a surface acoustic wave passing through the piezoelectric material.

The utilization of a bulk wave quartz crystal oscillator as a detector for gas chromatography is reported in King, W. H., "Using Quartz Crystals as Sorption Detectors ... Parts 1 & 2," *Research/Development,* 20, (4&5), at 28 (1969), and disclosed in U.S. Pat. No. 3,164,004 to King. In the foregoing, various coatings selective to interaction with a fluid to be analyzed were applied to said crystal. The interaction increased the effective weight of the coated crystal. Since surface acoustic wave characteristics are not significantly affected by changes in weight in a coated piezoelectric material through which the surface acoustic wave passes, there was no teaching in the foregoing that a surface acoustic wave was alterable via interaction of said coating with a substance to be analyzed.

STATEMENT OF THE INVENTION

It is an object of this invention to provide convenient and reliable methods capable of highly sensitive measurement of the properties of substances, such as fluids and polymers, to be analyzed.

It is a further object of this invention to provide said methods at a small cost relative to conventional detection methods.

It is another object of this invention to provide reliable highly sensitive apparati for monitoring of the various physical parameters of a substance, such as a fluid or polymer, said apparatus being of conveniently small size and low cost, relative to conventional apparati.

Additional objects and advantages of the invention will be evident from the following.

In accordance with the foregoing, the invention is in a method for detecting a substance, which comprises generating a surface acoustic wave in a piezoelectric material element coated on the surface through which the wave travels with a material selectively interactive with said substance; contacting said substance with the coating material thereby altering at least one property of the surface acoustic wave; and measuring the alteration of a wave property as an indication of the presence of the substance.

The invention is also in an apparatus for detecting a substance, which comprises a piezoelectric material element adapted for the travelling therethrough of a surface acoustic wave, coated on the surface through which the wave travels with a material selectively interactive with said substance, and disposed for contact of the coating material with said substance; oscillation-generating means operatively associated with the piezoelectric material element whereby a surface acoustic wave is induced in the coated surface; and detecting means operatively associated with the piezoelectric material element and adapted for measuring an alteration of a property of the wave.

The invention is also in a method of detecting information relating to a polymer, which comprises generating in a piezoelectric material element a surface acoustic wave; during the travelling of the surface acoustic wave through the piezoelectric material element, contacting a thin layer of the polymer with the surface through which the wave travels; subjecting the thin layer of polymer to a variation in environment during said contact thereby causing modification of a property of the polymer, whereby also a property of the surface acoustic wave is altered; and measuring said alteration in a wave property as an indication of the modification of the polymer property during the variation in environment.

The invention is further in an apparatus for detecting information relating to a polymer during a variation in its environment, which comprises a piezoelectric material element disposed and adapted for contact of a surface thereof with a thin layer of the polymer; contacting means operatively associated with the piezoelectric material element and adapted for maintaining contact between said surface of the material and the thin layer of polymer; oscillation-generating means operatively associated with the piezoelectric material element and adapted for inducing a surface acoustic wave in said surface of the piezoelectric material element; and detecting means operatively associated with the piezoelectric material element and adapted for measuring an alteration of a property of the surface acoustic wave.

The invention has the distinct advantage of operating via surface acoustic wave phenomena. The wave travels virtually unattenuated in solids, with velocities of some five orders of magnitude less than an electromagnetic wave. Further, the energy of the wave is confined to the surface of the material through which it travels; it is available there for sampling or alteration with tap electrodes. These properties make it possible to construct SAW delay lines and resonators which are small and very reliable, affording significant production and operation economies.

In addition, the invention affords a means of measuring parameters of various fluids and solids with a sensitivity not previously available at the significantly decreased cost, in both equipment and labor, of the claimed methods and apparati.

PREFERRED EMBODIMENTS OF THE INVENTION

A better understanding of the instant invention may be achieved with reference to the attached figures.

Figure 1:
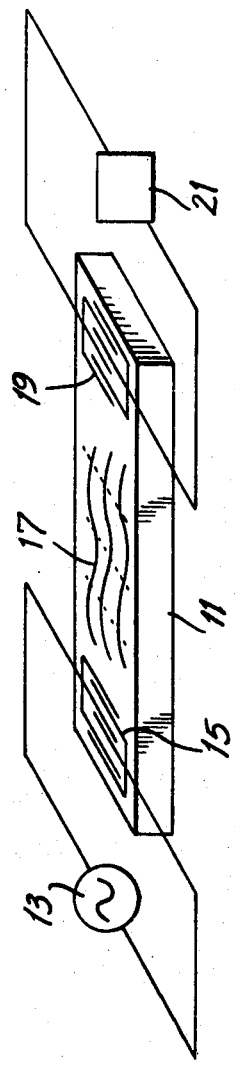
FIG. 1 is an illustration of a surface acoustic wave detection apparatus of the invention.

As illustrated in FIG. 1 piezoelectric material element 11 is provided to which is affixed an oscillation-generating means 13 at one end via interdigital electrodes 15. In operation, oscillation-generating means 13 induces a surface acoustic wave, shown diagrammatically at 17, in the piezoelectric material element 11. The interdigital electrodes 15 are transducers which convert an electrical signal into the surface acoustic wave which travels through the element 11. Interdigital electrodes 19 fixed at the other end of piezoelectric material element 11 reconvert the wave 17 into an electrical signal which is sensed by a suitable detection means 21.

A coating of an organic material 51 (not shown in this figure for purposes of clarity, but illustrated in FIG. 2) may be placed on the surface of element 11 through which wave 17 passes. This coating is selective to interaction with a substance to be detected. This interaction causes a modification of at least one property of the surface acoustic wave 17 which causes a corresponding alteration in the electrical signal into which the wave is converted by electrodes 19 and this change in the surface acoustic wave is detected by means 21.

The interaction, therefore, indicates the presence of said substance.

Figure 5:
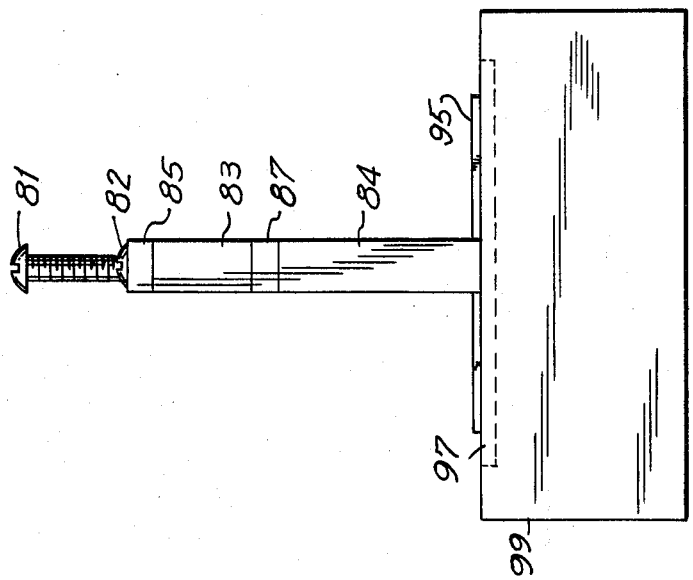
FIG. 5 is a side view of the device of FIG. 4 taken along line 5—5 of FIG. 4.

Alternatively, piezoelectric material element 11 may be placed in contact with a thin polymer layer 95 (as illustrated in FIG. 5) where a change in the thin layer induced by a variation in its environment will cause an alteration of the wave 17. The alteration will, again, be sensed by detection means 21, thereby affording a means for monitoring a property of the thin polymer layer.

By correlating the alteration of the electrical signal sensed by the detecting means with, for example, the temperature of the thin polymer layer, or with the time (e.g. from the beginning of the variation in the environment of the thin polymer layer) at which it occurs, properties of the polymer under various environmental influences can be detected.

Figure 2:
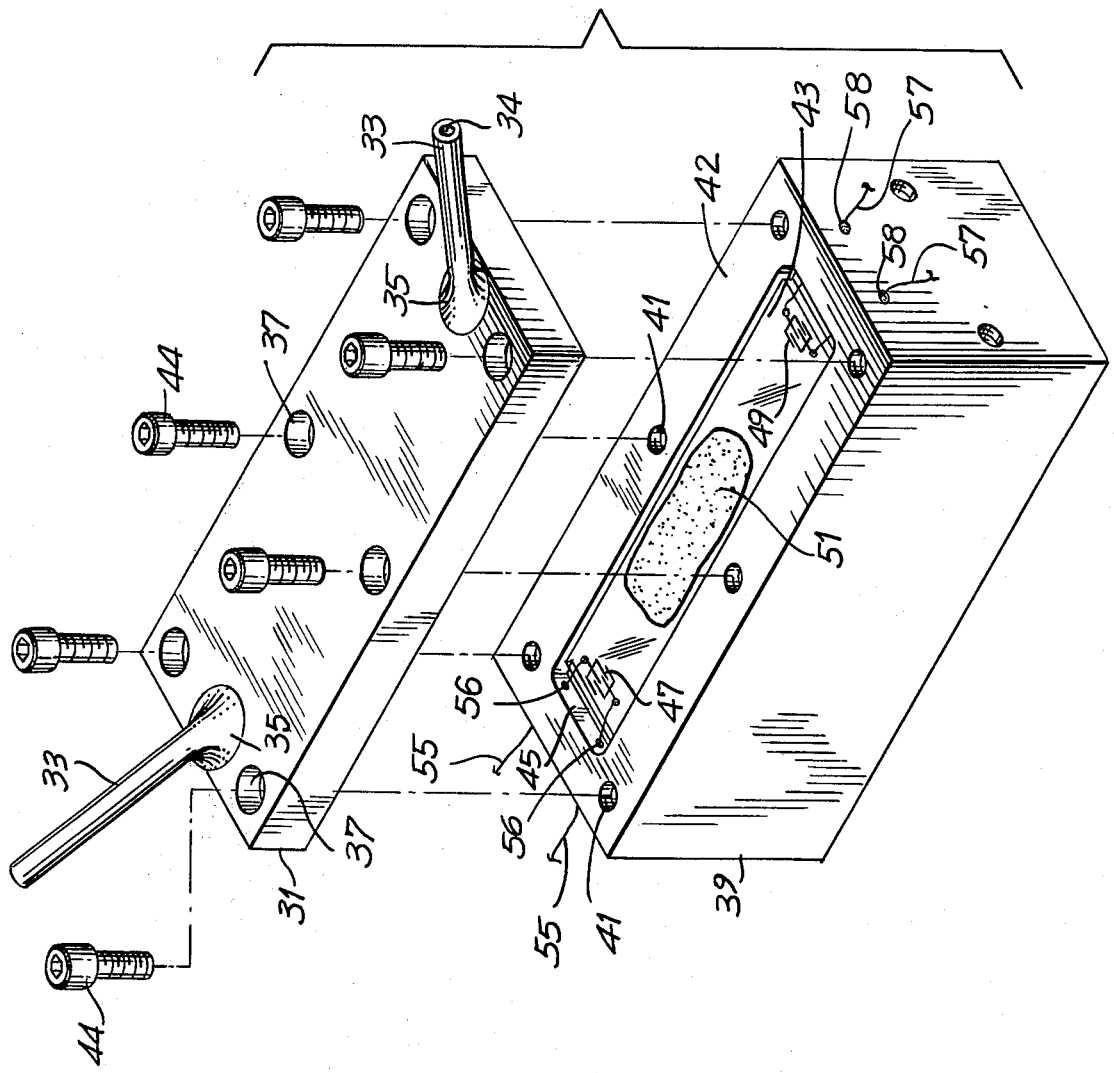
FIG. 2 is an exploded perspective view of a surface acoustic wave device in accordance with the invention.

Reference is now made to where one embodiment of the invention is shown in FIG. 2, which has cover 31 and block 39 which cooperate to form a housing. Cover 31 is preferably a flat stainless steel plate, typically approximately 0.125 inch in thickness. Tubes 33 are provided which project from opposed ends of the upper surface of the cover. Each tube 33 has a bore 34 therethrough which is substantially aligned with the longitudinal axis of the tube and the bore continues through cover 31 so as to form a communication passage through the cover. The tubes 33 are attached to the cover 31 by means of welds 35. Cover 31 also includes a number of holes 37 each adapted for the passage therethrough of a bolt 44 to secure the cover to block 39.

Block 39 is adapted to receive a quartz substrate piezoelectric material element 43 in a cavity 45 therein. The upper surface of block 39 includes threaded holes 41 about the peripheral portion 42 to threadably receive bolts 44 which pass through holes 37 in cover 31, thereby to attach the cover to the block. A pair of lead wires 55 and 57 are provided to pass through pairs of holes 56 and 58, respectively, in the opposed ends of block 39. One end of each lead wire 55 is fixed to interdigital electrodes 47 (lithographically deposited on piezoelectric material element 43) by conductive epoxy glue (of course, other known means, for example soldering, are also suitable). Electrodes 47 act as transducers to convert an electrical signal, emanating from an oscillation-generating means (not shown) and travelling through wires 55, into a surface acoustic wave travelling through piezoelectric material element 43. In like manner, one end of each lead wire 57 is fixed to interdigital electrodes 49 which act as transducers to reconvert the wave after it has travelled through the piezoelectric material element 43 into an electric signal which travels through wires 57 to a detecting means (not shown). A coating 51 of suitable material is placed on the piezoelectric material element 43. In the preferred embodiment, the material is Dow Corning 970 V vacuum grease. Alternatively, coating 51 may be a thin polymer film deposited on the surface.

In operation, the underside of the cover 31 and top of the block 39 abut one anther in a closed position so that the holes in each are aligned; bolts 44 pass thorough holes 37 and are threadingly engaged within holes 41. A gaseous substance to be analyzed passes through one of the tubes 33 through the cover 31 and into the cavity 45 containing the piezoelectric material element 43. The substance contacts the coating of material 51 and selectively interacts with the coating. In cooperation with this interaction, an electrical signal passes through wires 55 (from an oscillation-generating means) to interdigital electrodes 47 thereby inducing a surface acoustic wave in piezoelectric material element 43. The interaction of the substance with the coating 51 alters one or more properties of the wave and the altered wave is reconverted to an electrical signal at interdigital electrodes 49, and the signal flows through wires 57 to a detecting means which senses the alteration of the signal and, therefore, the alteration of the wave property. The alteration of the signal is, in view of the known identity of the coating 51, characteristic of the substance and establishes its presence.

Figure 3:
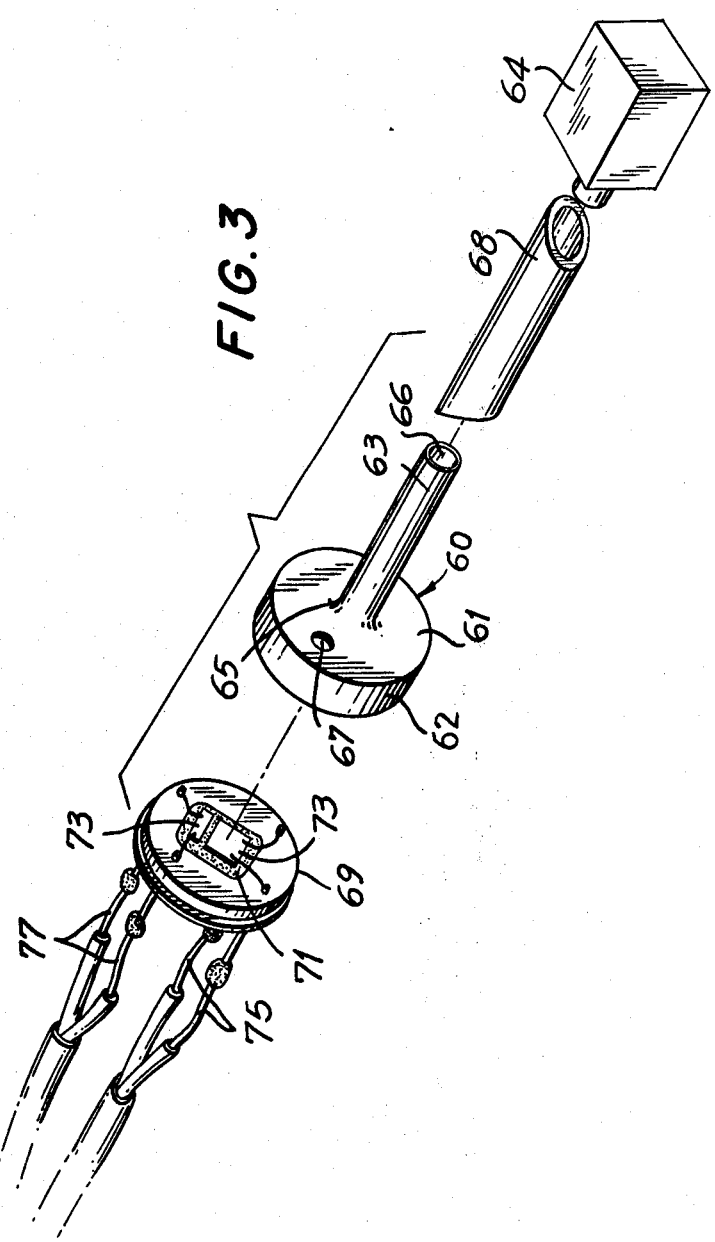
FIG. 3 is an exploded perspective view of another surface acoustic wave device in accordance with the invention.

In an alternative embodiment, the surface acoustic wave device is in part a modification of an apparatus intended for use as a spurious side band suppression filter for home TV video games as shown in FIG. 3. In this embodiment, a cover 60 and base 69 cooperate to form a housing.

The cover 61 includes a circular end wall 61 and a cylindrical side wall 62. A tube 63 having a through bore 66 substantially aligned with its longitudinal axis is welded, as at 65, to end wall 61. The bore continues through the cover 60 to form a communicating passage through the cover. End wall 61 of cover 60 also includes a hole 67 where the gaseous mixture to be analyzed may be exhausted. An adapter 68 is also provided which is a section of tube to fit sealingly over the free end of tube 63 and is attached at its other end to a source of the substance to be analyzed, in this case gas chromatograph 64.

Cover 60 fits over and sealingly engages base 69. Piezoelectric material element 71 is mounted on the circular face of base 69 which faces cover 60. RF interdigital transducers 73, fabricated from a chromium and gold alloy, are superimposed on the piezoelectric material element 71 and convert an electrical signal passing through wires 75 from an oscillation-generating means (not shown) into a surface acoustic wave in piezoelectric material element 71. The wave is reconverted into an electrical signal which passes, via wires 77, to a detecting means. A coating of material selective to interaction with a substance to be analyzed, or a thin layer of polymer which is itself to be analyzed, may be deposited on the piezoelectric material element 71.

In operation in an analyzing apparatus for detecting a substance the device of FIG. 3 is essentially analogous to the device of FIG. 2. The cover 60 and base 69 are engaged to form a housing and a chamber therein. The substance to be analyzed passes through tube 63 into the chamber between the inner circular face 61 of the cover 60 and the base 69 where it contacts the coating on the piezoelectric material 71. One or more properties of the surface acoustic wave are altered, and a corresponding alteration in the electrical signal reconverted from the wave is sensed by the detecting means. The alteration produces a response which is easily associated with a specific substance.

The apparatus described in FIG. 3 is, due to its potentially very small size, especially useful in gas chromatograph and other applications in which the presence of a substance is detected.

Figure 4:
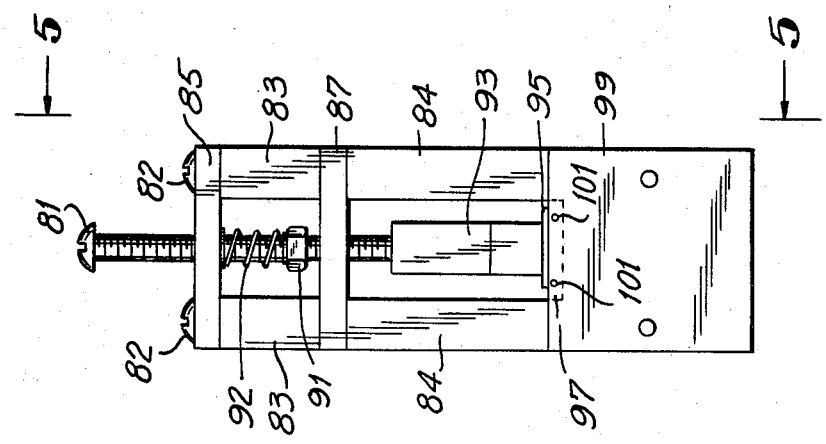
FIG. 4 is an end-view of a surface acoustic wave device including clamping means.

FIG. 4 is illustrative of a polymer film clamping system. In this embodiment the block 99 corresponds to that shown in FIG. 2 (save for the absence of coating 51). Mounted on block 99 is an assembly including first vertical spacing elements 83, second vertical spacing elements 84, a first cross-piece 85, a second cross-piece 87 and bolts 82 passing through and securing each of the foregoing. Bolts 82 are threadingly engaged by holes (not shown) around the periphery of block 99. A main bolt 81 passes through first cross-piece 85 and second cross-piece 87. A nut 91 is threadingly engaged on main bolt 81 so as to occupy a position intermediate between the first and second cross-pieces and a helical spring 92 is arranged about main bolt 81 so that one of its ends abuts a surface of nut 91 and the other end the bottom of first cross piece 85. The lower end of main bolt 81 abuts one end of a contact element 93, the other end of which abuts a thin polymer layer 95 on piezoelectric material element 97, which is shown in phantom. Lead wires (not shown) may connect the piezoelectric material element 97 with an oscillation-generating source (also not shown) and pass through access holes 101. As is evident from FIG. 5, the clamp may be arranged midway between the opposing ends of block 99.

In operation, main bolt 81 is tightened to apply pressure through contact element 93 to the thin polymer film 95, thereby bringing it into contact with piezoelectric material element 97. A surface acoustic wave is induced to travel through the piezoelectric material 97 by supplying an appropriate electrical signal thereto while, for example, the temperature around and of the thin polymer layer, for example, is increased. Typically, this may be effected with any suitably adaptable heat source placed in proximity of the polymer. The surface acoustic wave generated by the signal is influenced by the thin polymer layer. At the end of the piezoelectric material element 97 opposite that at which the wave is induced, the wave is reconverted to an electrical signal which is monitored by detecting means (not shown). When changes in the polymer due to increase in the temperature cause interaction with the surface acoustic wave and a property thereof to be altered, the corresponding alteration in the electrical signal fed to the detecting means is sensed. An alteration is matched with the temperature at which it occurs. At the maximum alteration, the temperature is the glass transition temperature of the polymer.

In viewing the invention it is important to recognize that a change in mass in the proximity of the interface between the surface of the piezoelectric material through which the wave travels and the material coating or polymer layer is not the determinative factor in the operation of the claimed invention. Instead, the operation of the claimed invention is dependent on the interaction of the surface acoustic wave with the coating or layer on the surface through which it travels. Inasmuch as the surface acoustic wave launches energy into the coating or polymer thin layer, the wave itself is affected by the speed at which sound travels in the coating or thin layer and by changes in the speed at which sound travels therethrough. A change in such speed (whether induced by interaction of the coating with a substance or by the modification of a thin polymer layer by a change in its environment) causes a measurable alteration of one or more properties of the wave. Additionally, changes in propagation velocity of the wave may also result from electrical interaction between the coating or thin layer and the surface wave. Thus, a change in the dielectric constant of the coating or thin layer will cause a change in the electrical interaction of same with the wave and a measurable change in a property of the wave.

For purposes of the invention, a material exhibits piezoelectric properties if it becomes electrically polarized when mechanically strained and, conversely, if mechanical strain therein results from the application of an electric field thereto. Examples of such materials suitable for practicing the invention are crystals especially such as quartz or lithium niobate, as well as barium titanate, lithium tantalate and $Bi_{12}GeO_{20}$.

The oscillation-generating means and detecting means may, for instance, be operatively associated with the piezoelectric material by electric connection via a transducer suitable for converting an electrical signal from the oscillation-generating means into a surface acoustic wave in the material and a second transducer adapted for sampling and reconverting the wave into an electrical signal. Low insertion loss and ease of impedance matching are desiderata by which the suitability of a transducer means may be evaluated.

An example of a suitable transducer is an arrangement of interdigital electrodes, for instance of a chromium/gold alloy or an aluminum alloy, which are deposited on the surface of the piezoelectric material through which the wave is to travel by a conventional photolithographic technique. Each transducer, for example, may consist of eight pairs of electrodes of one mil width spaced on two mil centers. The aperture of the fingers may be typically 106 mils and the center to center spacing of the two transducers about 1.8 inches. Another suitable transducer typically comprises the transversal (RF) filters described in connection with FIG. 3. The oscillation-generating means and detecting means are in all respects conventional.

The oscillation-generating means is typically a radio frequency (RF) power source which generates RF excitation power. This power source may comprise a commercially available quartz crystal oscillator and drive amplifier. Advantageously, a power levelled RF source may be used. The RF power from the power source may then be applied to the piezoelectric material through a suitable transducer to generate a surface acoustic wave, as previously described.

The detecting means may be adapted for measurement of the particular surface acoustic wave property of interest, for example frequency, amplitude or phase.

For a frequency measurement system the entire detection apparatus may be an oscillating circuit, the output of the oscillation-generating means being fed through the surface acoustic wave device back into the input of this means. Thus, the detecting means is one which monitors and records the frequency of the oscillation of the circuit. Typically, it is a binary counter interfaced with a computer or some other conventional calculating apparatus. The computer, for example, can easily determine the quiescent frequency of the circuit and substract this from subsequent readings to indicate frequency differences associated with substance/coating or polymer thin layer/surface interactions.

In an amplitude measurement scheme, the output of the oscillation-generating means may typically be fed into a zero-degree phase shift power splitter, which provides excitation for the two arms of a bridge circuit, one of which is the surface acoustic wave device and the other of which is a resistive attenuator. Thus, the detecting means includes the attenuator and two diode detectors of opposite polarity, one diode detector for the surface acoustic wave device and one for the attenuator. The signals from the detectors can be combined in a potentiometer to achieve a null. A slight alteration in the amplitude of the surface acoustic wave by a substance/coating interaction or a thin layer/surface interaction causes an easily detected shift in the balance of the bridge circuit. This information once again can be assimilated by an appropriately interfaced computer or like means.

In a phase measurement system, the same power splitter may direct the output of the oscillation-generating means to the surface acoustic wave device and to the attenuator (in parallel). The outputs of the surface acoustic wave device and the attenuator are fed to a double balanced mixer having local oscillator, radio frequency and intermediate frequency ports, the device being connected to one of the local oscillator and radio frequency ports and the attenuator to the other, and the intermediate frequency port being connected to an amplifier and ultimately interfaced with a computer or like means. The phase shift in the signal from the surface acoustic wave device (due to a previously described interaction) vis-a-vis the signal from the attenuator produces a measurable voltage change in the mixer signal especially when amplified, which may be assimilated by the computer or other means.

The substance-detection mode of the invention, i.e., substance-detection method and apparatus, is suitable for use with a fluid, or a fluid mixture, for example, one or more liquids, one or more gases and combinations thereof, and is especially suitable for the analysis of gas mixtures. The fluids and components of fluid mixtures may be organic or inorganic. Fluid mixtures of more than one organic component, such as dodecane in hexane, o-chlorotoluene in hexane, o-chlorotoluene in pentane and n-octane in hexane, are examples of suitable systems for analysis. However, fluid mixtures of inorganic substances and fluid mixtures of one or more organic and one or more inorganic components may also be analyzed. A commonly encountered inorganic substance is water.

It is not necessary that the substance-detection mode of the invention, or any other embodiment of the invention for that matter, be practiced under fluid-tight conditions. For example, if a fluid or fluid mixture to be analyzed is flowed past a surface acoustic wave device containing a piezoelectric material coated with a suitable material, the coating may interact with one or more individual components of the fluid or the fluid mixture, and the desired results be obtained, even though the device is open to the atmosphere. In fact, the atmosphere may be one or more of the components.

Thus, the substance-detection mode of the invention may be employed in connection with the analysis of exhaust emissions from combustion or other types of engines, for example automobile engines, by locating a surface acoustic wave device, which is connected to the balance of a detection apparatus in accordance with the invention, in proximity to an exhaust port of the engine for interaction with its exhaust, thereby detecting the composition of the exhaust as it passes the surface acoustic wave device. The detecting means of the detection apparatus may even operate as an integrator, in order to monitor cumulative emissions of one or more components of the exhaust over a period of time.

Of course, the invention may also be practiced in a substantially or completely fluid-tight environment. One such environment could be that provided by the arrangements illustrated in FIGS. 2 and 3 hereof, or any other suitable means which is substantially or completely impervious to the passage of fluid.

Additionally, it is recognized that an especially advantageous embodiment of this invention is a substance-detection method and substance detection apparatus including a plurality of surface acoustic wave devices, such as those of FIGS. 2 and 3. These embodiments employ more than one coated piezoelectric material element, preferably each coating material being selective to interaction with a substance different from each other substance with which the balance of material coatings is selectively interactive. This embodiment facilitates analysis of fluid mixtures having a plurality of components (substances) and/or the identification of an unknown substance, preferably flowed to the coatings. A subject substance interacts selectively with a coating material to alter a wave property in a corresponding element. Contacting of a plurality of substances with a plurality of coated elements may result in selective interaction with one or more coatings (since not all the substances may interact with the specific coatings selected. The interactions causing wave property alteration will indicate the presence of one or more substances. Findings may be based on a process-of-elimination analysis of the measurements indicating interactions or lack thereof between the various coatings and substance(s) for analysis.

The substance-detection mode is especially suitable for use in a gas chromotographic detection system. The elution from the chromotograph of one or more components of a fluid or fluid mixture injected into the chromotograph, in combination with a carrier gas, may be contacted with an appropriately coated piezoelectric material (which may, of course, be one of a plurality). If a coating is selective to a substance present, these interact thereby altering a surface acoustic wave which is measured by the detecting means according to the invention.

The particular material coating deposited on the piezoelectric material is dependent on the function which it must serve. For practical applications, a reasonably long residence time of such coating on the surface of the piezoelectric material is desirable. Therefore, a low vapor pressure material may be preferred, but is not absolutely necessary since the coating may easily be replaced or replenished. Further, the material coating must have the ability to interact with the particular substance to be analyzed. In this connection, the term "interact" is defined to include both chemical and physical phenomena. For instance, the component to be measured may react chemically with the material coating and/or be adsorbed thereon or absorbed therein. A coating may be organic or inorganic; some examples of suitable coatings for the method and apparatus of the invention include high molecular weight organosilicon greases such as Dow Corning 970 V vacuum grease (available commercially), squalane, high molecular weight aliphatic waxes such as Carbowax 20 M (available commercially), di-n-decyl phthalate, polycaprolactam, polyhexamethyleneadipamide, polypropylene, keratin (a polypeptide), polystyrene, polyvinylchloride and polycarbonate.

Since it is the interaction of the particular substance with the coating material that affects various properties of the surface acoustic wave passing through the piezoelectric material, it is important that appropriate coating materials be selected.

For example, in a system for measuring an alteration in the amplitude of a surface acoustic wave, the coating selective to interaction with a substance to be detected may be one which is plasticized (in a polymer sense) by the substance. Some suggested combinations of coating materials for various substances are as follows:

| Substance to be Detected | Coating Material |
| --- | --- |
| Halogenated hydrocarbon | Polypropylene |
| H$_2$O | Polycaprolactam |
| | Polyhexamethyleneadipamide |
| Low molecular weight polar organic compounds | Polycaprolactam |
| | Polyhexamethyleneadipamide |
| Low molecular weight aliphatic alcohols | Keratin |
| Ethyl benzene and other alkyl-substituted aromatic compounds | Polystyrene |
| Di-2-ethylhexylphthalate and other phthalates | Polyvinylchloride |
| Alkaryl hydrocarbons | Polycarbonate |

Also, in a system for measuring the frequency or phase of the surface acoustic wave, the coating may be one which undergoes a dielectric constant modification when interacted with the substance. Those skilled in the art will appreciate that the matching of substance(s) and coatings which interact to cause modification of the dielectric constant of the coating is relatively simple, and may be accomplished merely by contacting various substances and coatings and measuring the magnitude of changes in dielectric constant of the coatings. Some suggested combinations are:

| Substance to be Detected | Coating Material |
| --- | --- |
| Alkyl-substituted aromatic compounds | high molecular weight organosilicon greases |
| Alkyl hydrocarbons | high molecular weight organosilicon greases and high molecular weight aliphatic waxes |
| H$_2$O | polyhexamethyleneadipamide |

The comparison of interactions of various coating materials with a particular substance to be analyzed is facilitated by consideration of the ratio of the response of a detecting means with a coated piezoelectric material to said response with a clean piezoelectric material. This ratio is hereinafter termed the specificity index. For example, if the detecting means displays the response as a peak, the specificity index may be expressed in terms of the ratio of the peak-high generated by a coated piezoelectric material to the peak-high generated by a clean material for a given substance. The following table sets forth the specificity indices for some of the above-mentioned coatings with relation to interaction with o-chlorotoluene and n-octane.

| Specificity Indices for Coatings Investigated | | |
|---|---|---|
| | Specificity Index | |
| Coating Material | o-chlorotoluene | n-octane |
| Clean | 1.0 | 1.0 |
| Apiezon L | −3.5 | −2.6 |
| Carbowax 20M | −4.0 | 0.8 |
| Dow Corning 970V | −9.5 | −4.5 |

The Dow Corning 970V provides the greatest increase in sensitivity to o-chlorotoluene and n-octane while Apiezon L provides the smallest sensitivity increase. The Carbowax provides the greatest selectivity between o-chlorotoluene and n-octane as indicated by the differences in sign of the specificity indices.

The amount of coating applied to the piezoelectric material may vary within the practice of the invention. However, the amount of coating must not be so great as to interfere with wave propagation. The amount is, therefore, chosen for the best compromise.

The method of coating the piezoelectric material is not critical, provided the piezoelectric material remains undamaged. The coating should oscillate with the surface of the piezoelectric material during passage therethrough of the surface acoustic wave. Typically, the coating may be dissolved in a solvent such as acetone or chloroform to make a solution of several percent concentration by weight, the solution applied to the piezoelectric material, and the solvent allowed to evaporate, thereby leaving a coating of the previously dissolved material on the surface of the piezoelectric material. Of course, if the coating is a liquid at room temperature, it may be applied directly. Application with a cotton swab is suitable in many instances.

One or more alterations of properties of the surface acoustic wave, may be measured either separately or in various combinations. The measurement of a frequency-alteration of the surface acoustic wave is an especially advantageous embodiment of the substance-detection mode of the invention.

With reference to the polymer-related information-detection mode of the invention, i.e., the polymer-related information-detection method and apparatus, the polymer is deposited for testing on the piezoelectric material in a thin layer; the polymer may be in the form of a solid or in liquid solution. The thickness of the layer is, typically, in the order of about 0.01 to about 100 mils, preferably 10 mils, but the thickness of the layer is not critical to the invention as long as it does not uncontrollably interfere with the essential wave propagation in the piezoelectric material and monitoring of the wave.

Virtually any polymer is suitable for analysis with the invention. Examples are polyolefins, such as polyehtylene and polypropylene, polyesters, polypeptides, polyamides, polycarboxylic acids, polycarboxylates and polysulfones. Of course, the term "polymer" includes copolymers which are also ideal for analysis via the invention. Several additional specific examples of polymers which may be analyzed with the invention are bisphenol A polycarbonate, polysulfone, polytetrafluoroethylene, polyethylene terephthalate and polymethylmethacrylate.

If the polymer is applied to the piezoelectric material in solution, the solvent may be any material which will dissolve the polymer to be analyzed and, also, evaporate from the piezoelectric material. Such solvents are, typically, organic, for example alcohols and hydrocarbons with an appropriate boiling point.

The polymer, if in its solid form, may be maintained in contact with the piezoelectric material either by exerting pressure on the polymer via a convnetion contacting means, such as a clamp arrangement, or by casting the polymer in a thin layer on the surface of the piezoelectric material. Casting may be accomplished, for example, be depositing the polymer dissolved in a solvent on the piezoelectric material and allowing same to dry, or also by melt-casting. The manner in which contact is effected should not be destructive of the piezoelectric material.

The environmental changes to which the thin layer of polymer is subjected comprise a wide range of virtually all physical phenomena which may be continually or continuously varied to modify a property of the polymer. Examples of environmental changes, the effects of which on a polymer may be studied, are temperature variations, solvent evaporation therefrom and irradiation. Environmental changes may be induced by any suitably adaptable apparati, e.g., heaters, light sources, etc. Properties of the polymer which may be monitored are substantially all of those which can be modified by an environmental change and the alteration of which will cause a corresponding alteration in a property of the surface acoustic wave. An example of such properties is the elastic modulus of the thin layer of polymer.

Thus, in accordance with the polymer-related information-detection mode of the invention the determination of the glass transition profile of a polymer may be effected by generating a surface acoustic wave in a piezoelectric material, contacting a thin layer of the polymer with the piezoelectric material during the traveling of the wave therethrough, subjecting the thin layer to increasing temperature during said contact thereby causing a modification of a property (e.g. elastic modulus) of the polymer and an alteration of the property of the wave, and measuring a wave-property alteration and correlating it with the temperature at which it occurred. The glass transition temperature of the polymer may be determined by correlating the maximum alteration of a wave property with its corresponding temperature.

Further, a crystalline transition, other than a glass transition, may be monitored by contacting a thin layer of a polymer with a surface of a piezoelectric material through which a surface acoustic wave is traveling, subjecting the polymer to increasing temeprature which is below the glass transition temperature thereby causing a modification of a property (e.g. thermal expansion) of the polymer and an alteration of the surface acoustic wave, and measuring the alteration in a wave property and correlating same the with temperature or temperatures at which it occurs.

Also, the rate of solvent evaporation from a polymer may be determined via the practice of the invention by evaporating the solvent from the polymer during contact with the piezoelectric material through which is traveling a surface acoustic wave, and measuring alteration in a wave-property (e.g. elastic modulus) as an indication of the course of solvent evaporation. Correlation of the alteration(s) with the time elapsed during contact and evaporation is one effective monitoring scheme.

Additionally, photo-crosslinking of a polymer may be monitored by contacting a thin layer of the polymer with the surface of a piezoelectric material through with a surface acoustic wave is traveling subjecting the polymer to irradiation thereby causing crosslinking and alteration of a property (e.g. elastic modulus) of the surface acoustic wave, and measuring the alteration in a wave property as an indication of the extent of the crosslinking.

In connection with the polymer-related information-detection mode of the invention, the alteration of one wave property or a plurality of wave properties may be measured to determine desired information. For example, a phase alteration may be measured in combination with measurement of a frequency alteration or an amplitude alteration, or all three alterations may be measured. It is particularly advantageous to detect information by measuring amplitude and/or phase alterations of the surface acoustic wave.

EXAMPLE 1

(a) A 1% solution of o-chlorotoluene in hexane was introduced into a BENDIX model 2200 gase chromatograph which contained a six foot by ⅛ inch column of 3% OV-101 on Chromosorb W. The inlet temperature to the column was maintained at about 220° C. and helium was used as a carrier gas. The column was run isothermally at a 120° C. and at a flow rate of 15 ml/min. The elution from the gas chromatograph was conducted to a surface acoustic wave detecting apparatus containing a device as illustrated in FIG. 3 through a bridging sleeve of tubing attached at one end to the column and at the other end to the inlet tube of the device housing. The detecting apparatus was operated at room temperature and covered with glass wool to prevent drifting due to short term temperature fluctuations (e.g. drafts). It was adapted to measure frequency alterations and included a quartz crystal as the piezoelectric material. The oscillation-generating means of the apparatus comprised a three-stage RF amplification system operating as a preamplifier and power drive, including a model Ox-HI-OSC quartz crystal oscillator and PAX-1 drive amplifier, both of the International Crystal Manufacturing Company, and a buffer, all connected in parallel with the surface acoustic wave device. A pulse-shaping circuit was connected in series with the combined output of the foregoing and a 100-MHz counter in series with the pulse-shaping circuit (the gating period of the counter being determined by a crystal controlled time base with which selectable periods ranging from 0.01 to 10 seconds were available). The counter was interfaced with an LSI-11 microcomputer through a standard parallel interface module. Process data was displayed in real time on an XY plotter, a permanent record of the experiment being obtained easily therefrom.

Figure 6:
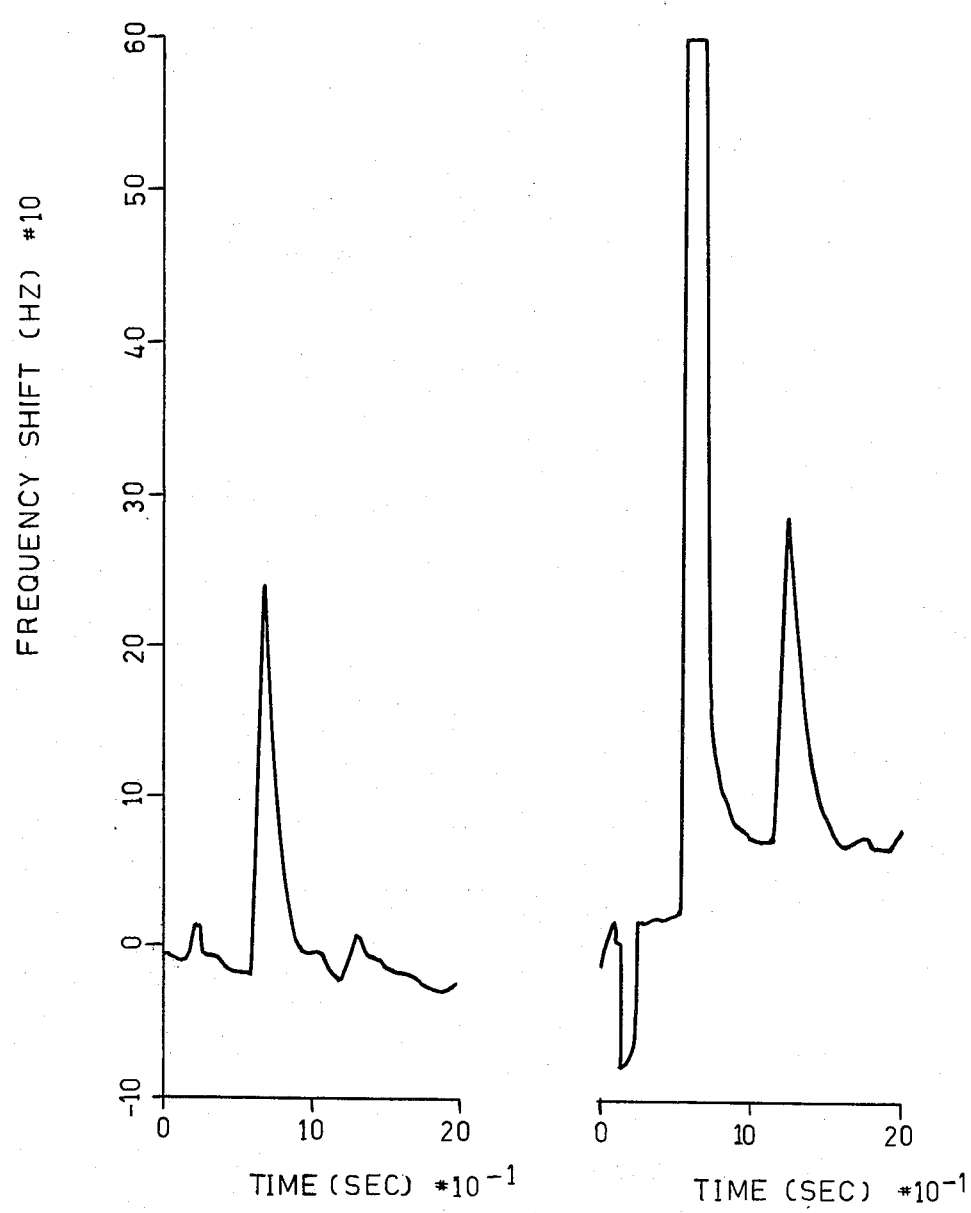
FIG. 6 is a comparative display of gas chromatographic peaks as measured by a surface acoustic wave method.

The elution from the gas chromatograph was fed into the surface acoustic wave detecting apparatus, the piezoelectric material being uncoated. The result was as illustrated in the left-hand portion of FIG. 6. The main peak corresponded to hexane and the small peak corresponded to o-chlorotoluene.

(b) In a second run, using the same procedure, the selectivity of the foregoing apparatus was enhanced by coating (with a cotton swab) the quartz with DC 970 V vacuum grease. Once again, the elution from the gas chromatograph was fed into the surface acoustic wave device and the result subsequently displayed. The significantly increased sensitivity of the device is evident from the right-hand portion of FIG. 6, the larger peak once again representing the hexane contribution and the smaller peak representing the o-chlorotoluene contribution.

EXAMPLE 2

Figure 7A:
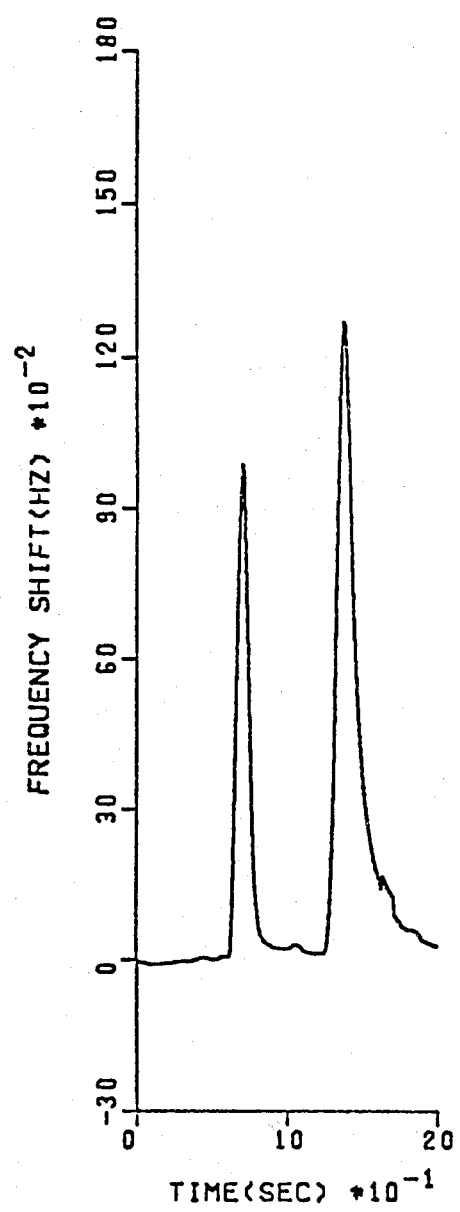
FIGS. 7a, 7b and 7c are a display of gas chromatographic peaks due to frequency alteration caused by various fluids in contact with coated lithium niobate.
Figure 7B:
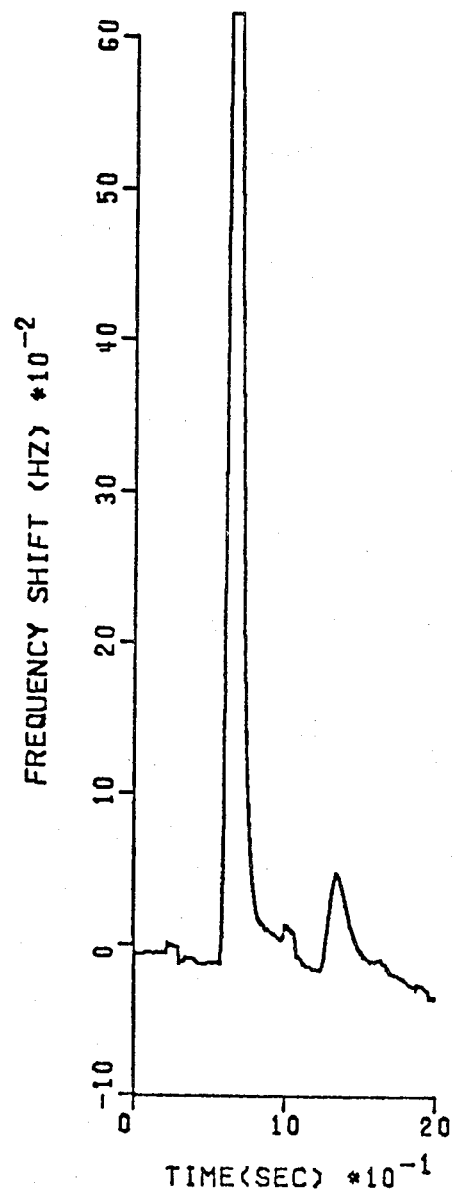
Figure 7C:
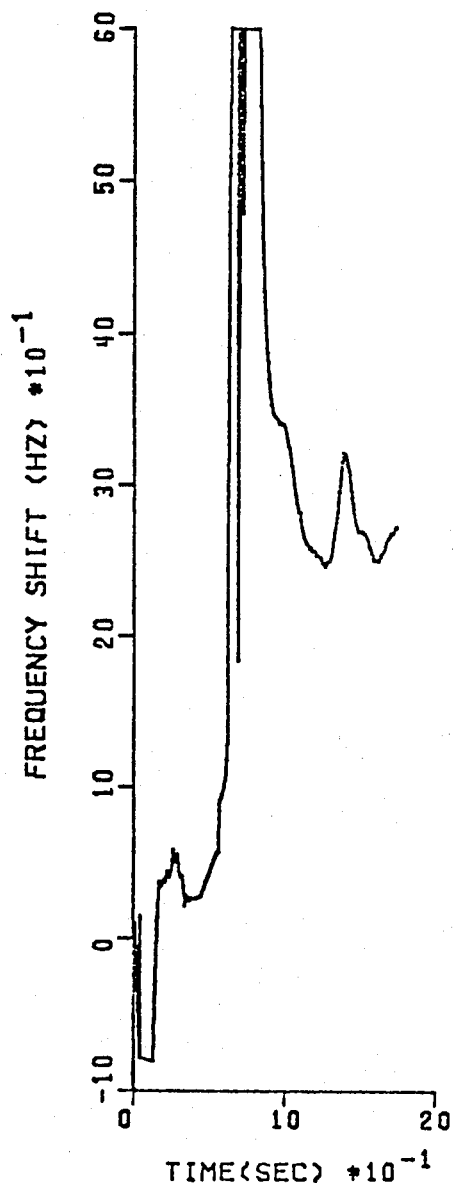

In accordance with the procedure set forth in Example 1(b), and using the same apparatus except for the replacement of the quartz crystal by a lithium niobate substrate, a series of one microliter injections of solutions containing 1%, 0.1% and 0.01%, respectively, of o-chlorotoluene in pentane were analyzed. Each of the injections was introduced into the gas chromatograph. At a column temperature of 120° C. and a flow rate of 15 ml/min, the results obtained with the detecting apparatus for the 1% solution are illustrated in FIG. 7A, for the 0.1% solution in FIG. 7B and for the 0.01% in FIG. 7C. It is noteworthy that in FIG. 7A the o-chlorotoluene peak is greater than the pentane peak even though the pentane was present in almost one hundred fold greater concentration. The sensitivity of the claimed invention in detecting substances at low concentrations is emphasized by the fact that FIG. 7C establishes the detection of about 100 nanograms of o-chlorotoluene (the smaller, second peak).

EXAMPLE 3

Figure 8:
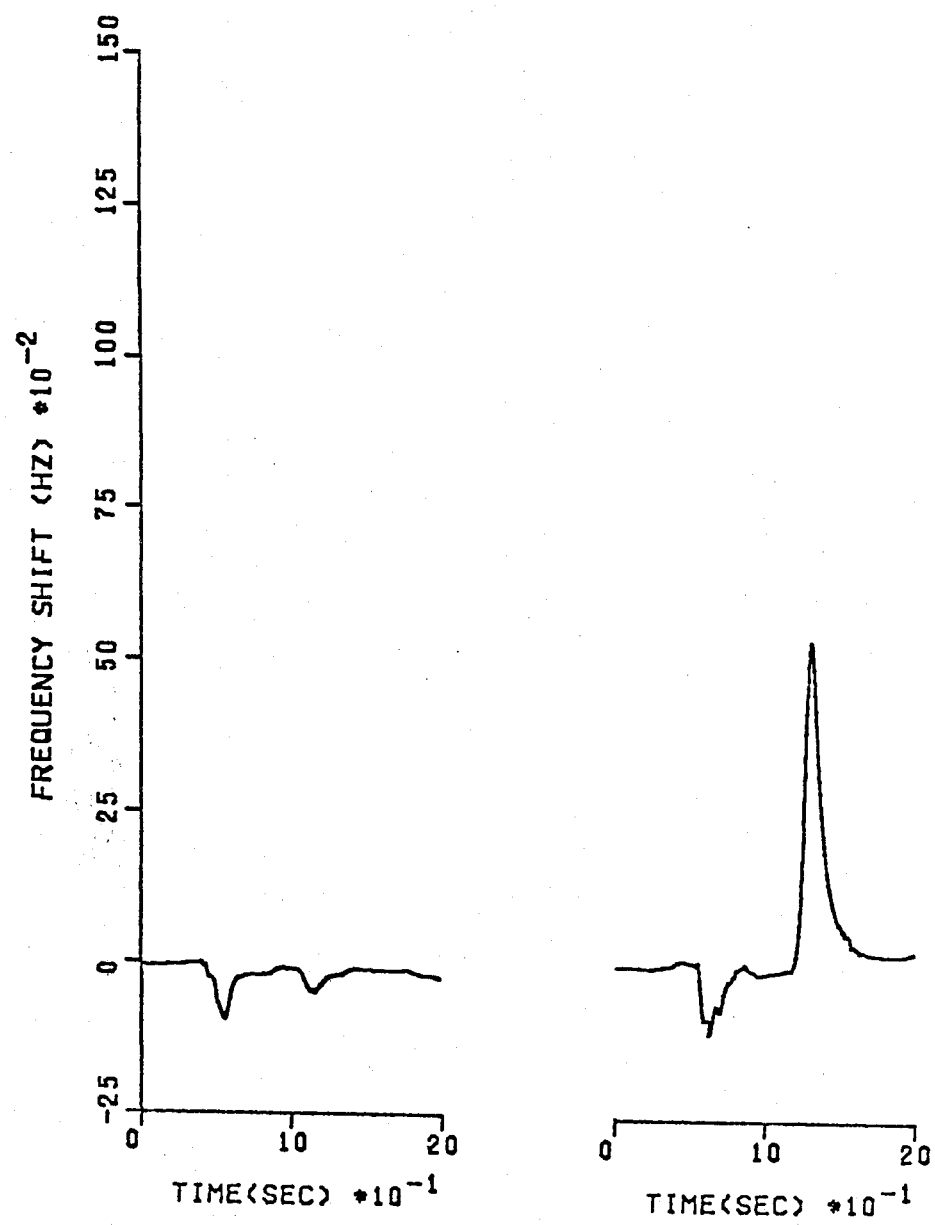
FIG. 8 is a comparative display of peaks due to frequency alteration caused by contact of various fluid mixtures with coated lithium niobate.

Employing lithium niobate as the piezoelectric material and Carbowax 20M as the coating, two runs otherwise in accordance with the procedure and apparatus described in Example 1(b) were performed with a 1% n-octane in hexane solution and a 1% o-chlorotoluene in hexane solution, respectively. The n-octane solution was relatively non-polar and the o-chlorotoluene solution relatively polar. AS is illustrated in FIG. 8, a dramatic manifestation of specificity due to the presence of the coating on the lithium niobate was observed; the non-polar compounds, i.e., n-octane and the hexane solvent, caused frequency shifts in the negative direction (left-hand display) while the polar o-chlorotoluene caused a shift in the opposite direction (right-hand display).

EXAMPLE 4

A block as illustrated in FIG. 2 was employed in combination with a clamp as a surface acoustic wave device, as illustrated in FIGS. 4 and 5. The clamp secured a polyethylene terephthalate film to a quartz crystal, providing a reproducible contact force. The surface acoustic wave device was integrated into an amplitude measurement system comprising an RF power source including a model Ox-HI-OSC quartz crystal oscillator and PAX-1 drive amplifier, both of the International Crystal Manufacturing Company, and a linear amplifier connected in series with a zero-degree phase shift power splitter, the splitter being connected in series with a unit comprising (1) the surface acoustic wave device, two RF amplifiers and a diode detector (in series) and (2) (also in series) an RF step attenuator with a diode detector, in parallel with unit (1). An LSI-11 microcomputer was interfaced with the foregoing.

The polymer film (polyethylene terephthalate) was pressed to about 10 mils thick and about ⅛ inch in diameter and mounted on the surface of the quartz. The RF power level was adjusted to provide about 9.5 volts of DC signal.

Figure 9:
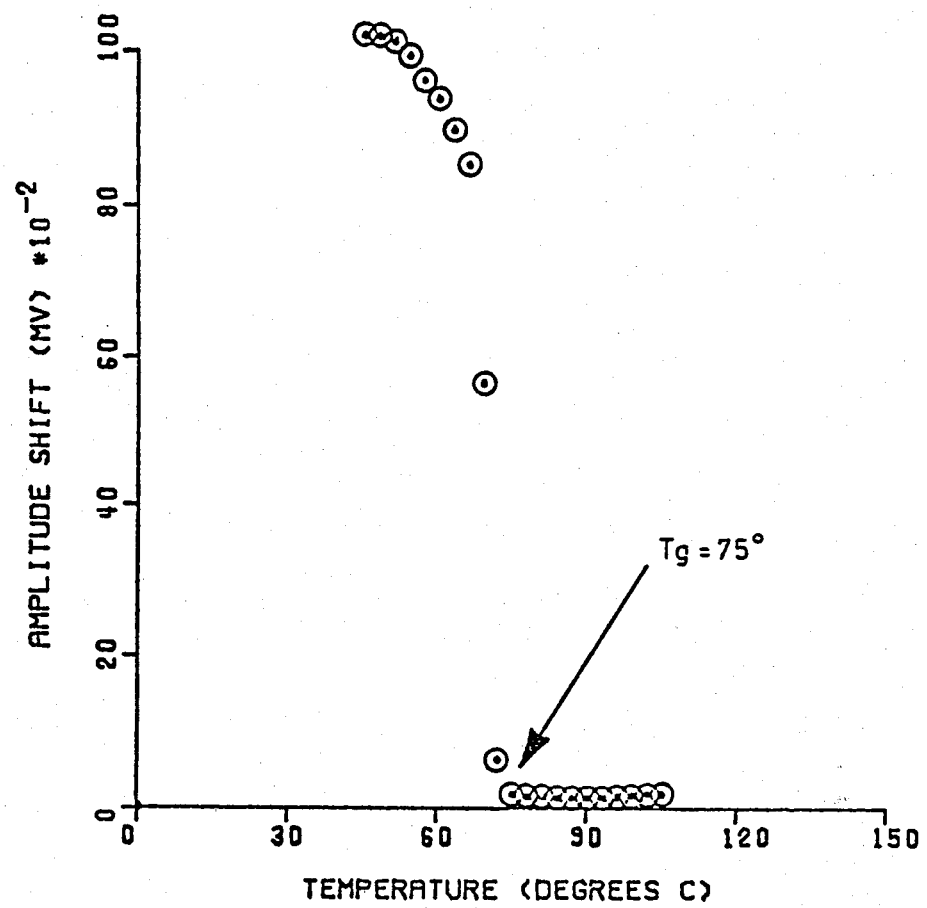
FIG. 9 is polyethylene terephthalate glass transition profile obtained with the invention.

To monitor the glass transition profile of polyethylene terephthalate, the temperature was increased in increments of 3° C. at a rate of 1.5° per minute. As the temperature of the environment increased, the polyethylene terephthalate film began to soften and adhere to the quartz, thereby attentuating the surface acoustic wave traveling through same. At 75° C. the wave was almost completely attenuated as shown by the discontinuity in the amplitude vs. temperature profile illustrated in FIG. 9. The point of discontinuity provides a clear indication of the glass transition temperature of polyethylene terephthalate.

EXAMPLE 5

Figure 10:
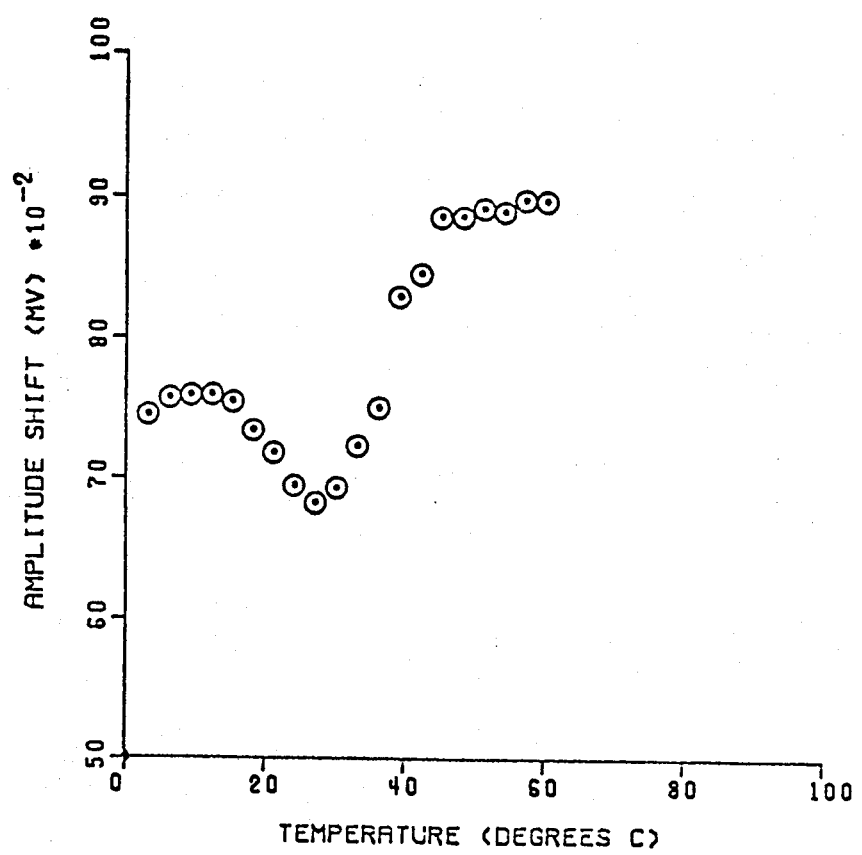
FIG. 10 is a display representing a Teflon crystalline transition obtained with the invention.

A run to monitor crystlline transitions in a polymer was performed in accordance with the procedure of Example 4, using the apparatus thereof except that a film of TEFLON was employed and the temperature was increased from about 10° to 27° C., below the glass transition temeprature of TEFLON. The results are illustrated in FIG. 10. As can be seen, a substantial signal was obtained with the maximum attenuation of the surface wave occurring at a temperature of approximately 27° C. This run was significant inasmuch as the crystalline transition of TEFLON is subtle and not easily observable. Nevertheless, with the claimed invention an accurate and easily interpretable indication of the transition was obtained; the indication can be correlated with the changes in linear expansion coefficient observed at the foregoing temperatures.

EXAMPLES 6

Figure 11:
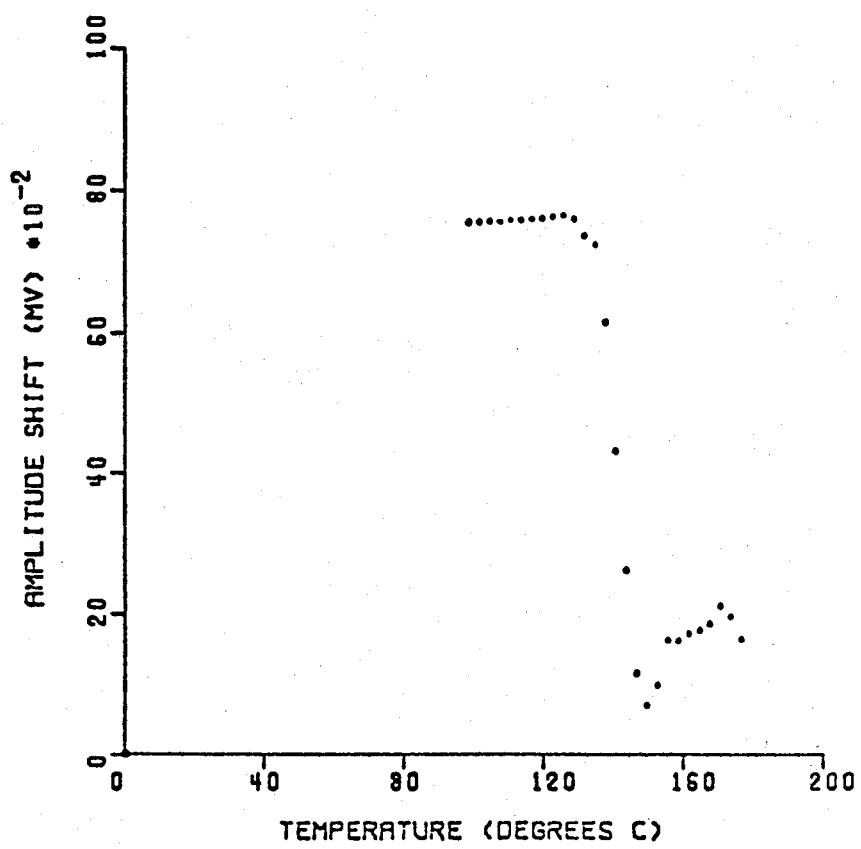
FIG. 11 is a glass transition profile of a polymethylmethacrylate cast film obtained with the invention.

The procedure of Example 4 was followed, with the apparatus described therein, save for the following exception: the clamp was dispensed with and a thin film of polymethylmethacrylate (PMMA) was cast on the quartz instead of clamped thereto. The film contained about 200 micrograms of the polymer and covered a circular area on the quartz of about 9 mm in diameter. The film was approximately 0.1 mil thick. FIG. 11 illustrates the results obtained in a study of the glass transition properties of PMMA. The discontinuity occurring at approximately 150° C. clearly indicates the temperature at which glass transition occurs. The temperature indicated is in accordance with and verifies the glass transition shift predicted by conventional theory due to the intimate contact of the PMMA with the quartz as a result of the casting mode.

EXAMPLE 7

Figure 12:
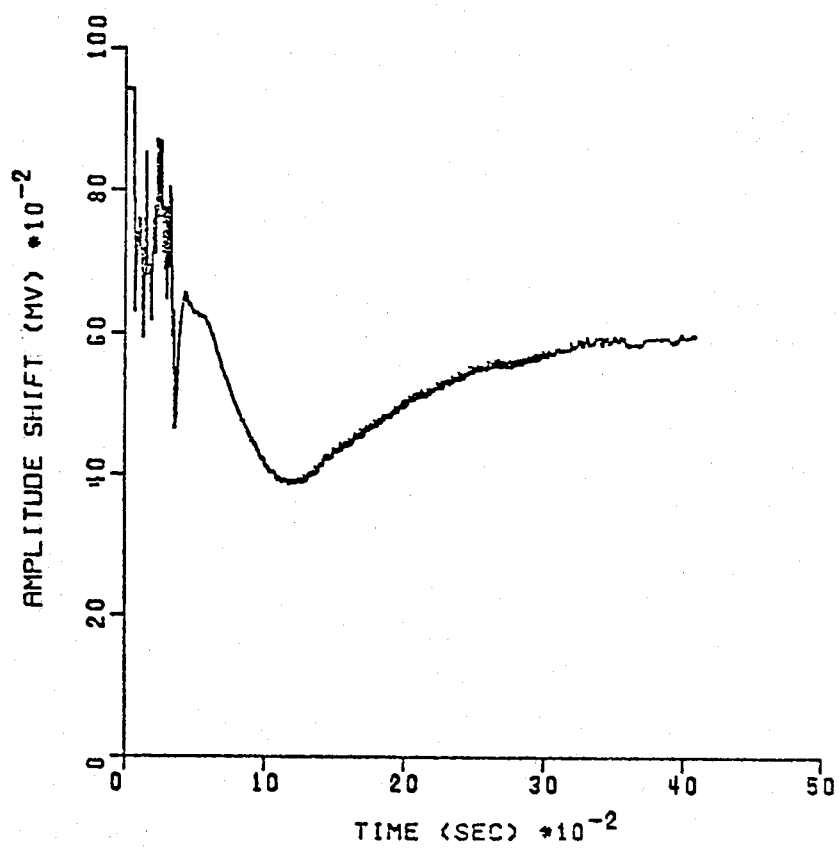
FIG. 12 is a display indicating the course of solvent evaporation from a spot of KPR photoresist, as obtained with the invention.

Another example of the utility of the claimed invention is the monitoring of the properties of KPR photoresist during the evaporation of a solvent therefrom. A drop of KPR was placed on the surface of the quartz of the surface acoustic wave device described in the previous example. The result of the effect of solvent evaporation on the amplitude of the surface acoustic wave is illustrated in FIG. 12. During the first 500 seconds, wild oscillations in the surface wave amplitude were recorded. Visual inspection of the surface at this time revealed that the spot appeared wet with solvent. These wild oscillations were most likely caused by interference effects as the film thickness changed due to solvent loss. A compressional wave was launched into the photoresist solution and probably partially reflected back into the surface from the photoresist/air boundary. This would have caused constructive and destructive interference effects to be observed as the boundary distance changed. The end of the period of wild oscillations was coincident with the spot appearing dry. However, the amplitude response continued to change until it stabilized after about 5,000 seconds, indicating that until that time other processes continued in the photoresist film.

Solvent evaporation rate during the baking of photoresist can have a significant effect on the quality of the film. Therefore, direct information about film behavior is important to obtain. Whereas conventional techniques which employ microbalance monitoring of bulk photoresists have not provided such information, the application of the claimed invention permits investigation of the solvent evaporation rate to be performed with films that are the same thickness as those used in practice.

EXAMPLE 8

Figure 13:
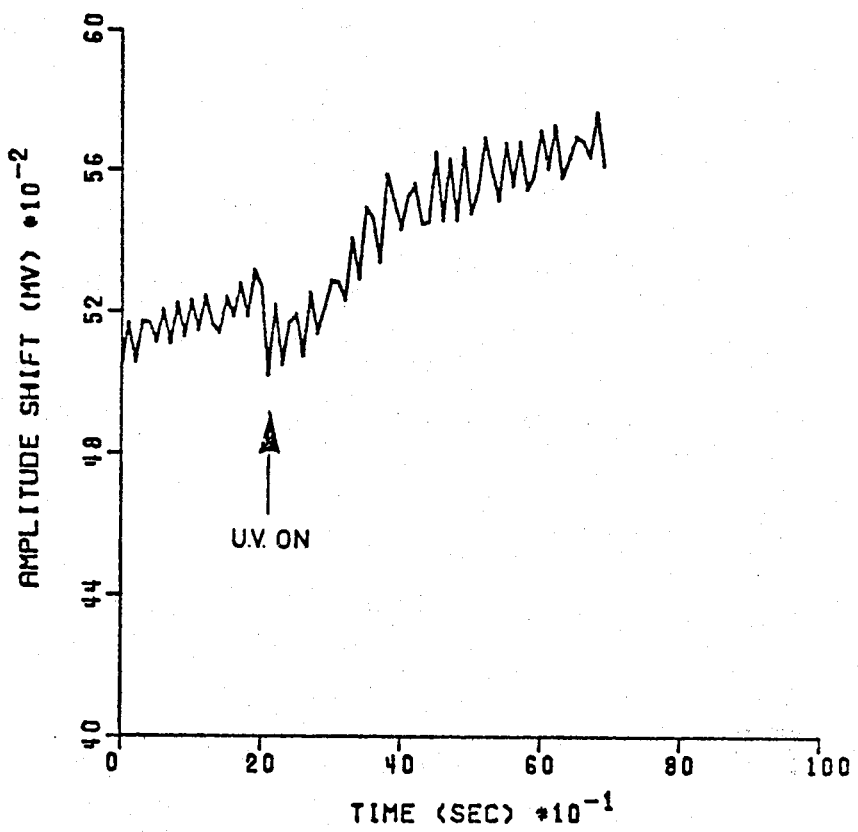
FIG. 13 is a display representing the effects of ultraviolet irradiation on KPR photoresist, as obtained with the invention.

The KPR photoresist deposit left on the quartz subsequent to evaporation as described in the previous example was irradiated with ultraviolet light so that the effects of photocrosslinking of the resist (due to the irradiation) could be studied. When polymers are crosslinked the effect is to make them more brittle. Thus, as crosslinking increased and the photoresist became more brittle, the attenuation of the wave was reduced inasmuch as the crosslinked photoresist interacted less with quartz through which the wave passed. After about 300 seconds the attenuation of the amplitude of the surface acoustic wave ceased and the signal levelled off as illustrated in FIG. 13.

It is thus seen that the invention provides a highly sensitive and relatively inexpensive measurement of various properties of fluids and solids by the employment of surface acoustic wave phenomena in physical probe applications, i.e., the monitoring of the influence on a surface acoustic wave of a material the properties of which are changing due to interaction with another substance or due to variation in its environment.

What is claimed is:

1. A method detecting information relating to a polymer which comprises generating in a piezoelectric material element a surface acoustic wave; during the traveling of the surface acoustic wave through the piezoelectric material element, contacting a thin layer of the polymer with the surface through which the wave travels; subjecting the thin layer to a variation in environment during said contact thereby modifying a property of the polymer and changing either or both of the velocity of sound in, and a dielectric property of, the polymer so as to alter one or more of the frequency, amplitude and phase of the surface acoustic wave; and measuring said alteration as an indication of the modification of the polymer property during the variation in environment.

2. A method as defined in claim 1, wherein an alteration in the amplitude of the surface acoustic wave is measured.

3. A method as defined in claim 1, wherein an alteration in the phase of the surface acoustic wave is measured.

4. A method as defined in claim 1, wherein the thin layer of polymer is about 10 mils thick.

5. A method as defined in claim 1, which comprises clamping the thin layer of the polymer to the surface of the piezoelectric material.

6. A method as defined in claim 1, which comprises casting the thin layer of the polymer on the surface of the piezoelectric material.

7. A method of detecting the glass transition temperature of a polymer, which consists essentially of generating in a piezoelectric material element a surface acoustic wave; during the traveling of the surface acoustic wave through the piezoelectric material element, contacting a thin layer of the polymer with the surface through which the wave travels; subjecting the thin layer of the polymer to increasing temperature during said contact, thereby changing either or both of the velocity of sound in, and a dielectric property of, the polymer so as to alter one or more of the frequency, amplitude and phase of the surface acoustic wave; and measuring the maximum alteration and correlating it with the temperature at which said maximum alteration occurred.

8. A method of detecting the rate of solvent evaporation from a polymer which consists essentially of generating in a piezoelectric material element a surface acoustic wave; during the traveling of the surface acoustic wave through the piezoelectric material element, contacting the polymer, in solution with a solvent, with the surface through which the travels; evaporating the solvent, thereby changing either or both of the velocity of sound in, and a dielectric property of, the polymer or polymer solution so as to alter one or more of the frequency, amplitude and phase of the surface acoustic wave; and measuring said alteration as an indication of the course of solvent evaporation.

9. A method of monitoring photo-crosslinking of a polymer, which consists essentially of generating in a piezoelectric material element a surface acoustic wave; during the traveling of the surface acoustic wave through the piezoelectric material element, contacting a thin layer of the polymer with the surface through which the wave travels; subjecting the thin layer of the polymer to irradiation thereby causing crosslinking of the polymer and changing either or both of the velocity of sound in, and a dielectric property of, the polymer so as to alter one or more of the frequency, amplitude and phase of the surface acoustic wave; and measuring said alteration as an indication of the extent of said crosslinking.

10. A method of detecting a crystalline transition in a polymer, which consists essentially of generating in a piezoelectric material element a surface acoustic wave; during the traveling of the surface acoustic wave through the piezoelectric material element, contacting a thin layer of the polymer with the surface through which the wave travels; subjecting the thin layer of polymer to increasing temperature which is below the glass transition temperature during said contact thereby changing either or both of the velocity of sound in, and a dielectric property of, the polymer so as to alter one or more of the frequency, amplitude and phase of the surface acoustic wave; and measuring said alteration and correlating same with the temperature or temperature range at which it occurs.

11. A surface acoustic wave apparatus for detecting information relating to a polymer during variation in its environment, which comprises a piezoelectric material element disposed for contact of a surface thereof with a thin layer of the polymer; contacting means operatively associated with the piezoelectric material element and adapted for maintaining contact between said surface and the thin layer of polymer; oscillation-generating means operatively associated with the piezoelectric material element to induce a surface acoustic wave in said surface of the piezoelectric material element; and detecting means operatively associated with the piezoelectric material element and adapted for measuring alteration of one or more of the frequency, amplitude and phase of the surface acoustic wave due to modification of a property of the polymer and concomitant change in either or both of the velocity of sound in, and a dielectric property of, the polymer.

12. A surface acoustic wave detection apparatus as defined in claim 11, wherein the piezoelectric material is selected from the group consisting of quartz and lithium niobate.

13. A surface acoustic wave detection apparatus as defined in claim 11, wherein the contacting means is clamping means.

14. A surface acoustic wave apparatus for detecting information relating to a polymer during a change in its environment, which comprises a block having in one of its faces a cavity adapted for receiving a piezoelectric material element; a piezoelectric material element mounted in said cavity and disposed for contact of a surface thereof with a thin layer of the polymer; clamping means mounted on said block and operatively associated with the piezoelectric material element and adapted for maintaining contact between said surface and the thin layer of polymer; a first transducer which interfaces with the piezoelectric material element; a second transducer interfacing with said element and adapted to sample a surface acoustic wave traveling therethrough and convert same to an electrical signal; oscillation-generating means electrically connected to said first transducer to induce a surface acoustic wave in said surface of the piezoelectric material element; and detecting means electrically connected to said second transducer, said detecting means being adapted for measuring alteration in the electrical signal from the second transducer corresponding to an alteration of one or more of the frequency, amplitude and phase of the surface acoustic wave due to modification of a property of the polymer and concomitant change in either or both of the velocity of sound in, and a dielectric property of, the polymer.

15. A surface acoustic wave detecting apparatus as defined in claim 14, wherein said transducer and second transducer each is an interdigital electrode abutting said piezoelectric material element.

16. A surface acoustic wave detecting apparatus as defined in claim 14, wherein the transducer and second transducer each is of aluminum or a chromium and gold alloy.

* * * * *